United States Patent [19]

Lefebvre

[11] Patent Number: 5,421,832
[45] Date of Patent: Jun. 6, 1995

[54] FILTER-CATHETER AND METHOD OF MANUFACTURING SAME

[76] Inventor: Jean-Marie Lefebvre, 219, boulevard de la liberté, 59800 Lille, France

[21] Appl. No.: 242,038

[22] Filed: May 12, 1994

Related U.S. Application Data

[63] Continuation of Ser. No. 899,213, Jun. 16, 1992, abandoned, which is a continuation-in-part of Ser. No. 610,414, Nov. 7, 1990, abandoned.

[30] Foreign Application Priority Data

Dec. 13, 1989 [FR] France ............................ 89 17201

[51] Int. Cl.⁶ .................................................. A61M 31/00
[52] U.S. Cl. ........................................ 604/53; 604/104; 604/107; 264/DIG. 48; 264/DIG. 66; 606/191
[58] Field of Search ................. 604/53, 95, 190, 280, 604/104–109; 606/190, 191; 128/772, 898; 264/DIG. 66, DIG. 48, 340, 345

[56] References Cited

U.S. PATENT DOCUMENTS

| | | | |
|---|---|---|---|
| 1,719,428 | 7/1929 | Friedman | 604/105 |
| 1,863,057 | 6/1932 | Innes | 604/105 |
| 3,938,530 | 2/1976 | Santomieri | 604/105 |
| 4,571,241 | 2/1986 | Christopher | 604/104 |
| 4,608,965 | 9/1986 | Anspach, Jr. | 604/105 |
| 4,699,611 | 10/1987 | Bowden | 604/105 |
| 4,739,762 | 4/1988 | Palmaz | 604/104 |
| 4,807,626 | 2/1989 | McGirr | 604/107 |
| 4,808,163 | 2/1989 | Laub | 604/105 |
| 4,995,868 | 2/1991 | Brazier | 604/104 |

FOREIGN PATENT DOCUMENTS

| | | | |
|---|---|---|---|
| 2606642 | 5/1988 | France | |
| 0955490 | 4/1964 | United Kingdom | 604/105 |

OTHER PUBLICATIONS

Smith et al., "Stamey Catheter Kit" Radiology 139:230–231, Apr. 1981.

*Primary Examiner*—C. Fred Rosenbaum
*Assistant Examiner*—Ronald K. Stright, Jr.
*Attorney, Agent, or Firm*—Ladas & Parry

[57] ABSTRACT

This invention relates to a filter for the partial and at least temporary interruption of a vein, comprising a tube made of polytetrafluoroethylene presenting towards its distal end longitudinal notches distributed symmetrically over its periphery and defining flexible bands, and a conduit made of polytetrafluoroethylene inside the tube; the conduit and the tube are joined for example by thermo-welding by their distal ends. A ring made of a radio-opaque material is preferably included between the distal ends during thermo-welding. The flexible bands open out transversely by the conduit sliding in the tube. They have undergone a treatment of thermo-setting, memorizing in the polymeric structure of the tetrafluoroethylene the opened out form and/or a helical form.

1 Claim, 3 Drawing Sheets

FILTER-CATHETER AND METHOD OF MANUFACTURING SAME

This is a continuation of application Ser. No. 07/899,213 filed on Jun. 16, 1992, now abandoned, which is a continuation-in-part application of U.S. Ser. No. 07/610,414, filed on Nov. 7, 1990, now abandoned.

FIELD OF THE INVENTION

The present invention relates to a filter for medical use, adapted to stop the blood clots circulating in a vein, and to the catheter for introducing it into the vein. More especially, it relates to a filter whose use is temporary, i.e. which may be withdrawn from the vein when the treatment administered to the patient is judged satisfactory and the presence of the filter is no longer justified.

BACKGROUND OF THE INVENTION

Such temporary filters are known, particularly by Patent FR-A-2 580 504. They are fixed to the distal end of a catheter for introduction and their structure is such that, during introduction into the vein, the elements ensuring filtration are folded into a sheath extending the catheter, and, when the filter has been placed in the vein, said filtering elements open out according to remotely controlled means. In the filter of FR-A-2 580 504, the filtering means are legs which extend, at rest, approximately parallel to one another along the generatrix of a cylinder and the means for opening them out are reversible expansion means located inside the cylinder defined by the filtering legs; by deformation, the expansion means exert on the legs a thrust from the inside so as to open them out in the manner of the spokes of an umbrella, by a sufficient amplitude for each leg to be applied at least in its distal zone against the wall of the vein.

These known filters present two drawbacks: On the one hand, they necessitate a complementary sheath for protecting the filtering legs, arranged at the distal end of the catheter, and adapted to be withdrawn when the filter is opened out in the vein. On the other hand, they require complementary, complex expansion means for opening out the filtering elements, remotely controllable in reversible manner, for example an inflatable balloon with a conduit supplying the corresponding fluid. This renders the structure of the filter and catheter assembly complex and delicate.

In order to overcome the drawbacks set forth hereinabove, document FR-A-2 606 642 proposes a filtering element which is borne at the distal end of the catheter and which comprises a plurality of flexible legs; the opposite ends of these flexible legs are interposed between two members joined together by a means for modifying the relative positions thereof, with the result that approach of the two members along the longitudinal axis provokes the transverse expansion of the flexible legs.

One embodiment cited in document FR-A-2 606 642 provides that the flexible legs result from the cut-out of the tube constituting the distal part of the catheter, said distal part being fast with an inner conduit which may slide longitudinally inside the tube.

This embodiment is particularly simple.

However, Applicant has observed that the presence of such a filter-catheter in a vein might cause blood clots to appear, localized in the immediate proximity of said filter.

It is an object of the present invention to propose a filter-catheter of the type mentioned above, which overcomes the drawback observed.

SUMMARY OF THE INVENTION

This object is attained perfectly well by a filter for partial and at least temporary interruption of a vein, which comprises a tube presenting, towards its distal end, longitudinal notches distributed symmetrically over its periphery, and defining flexible bands, and a conduit inside said tube and fast therewith by its distal end. According to the invention, the tube and the inner conduit are both made of polytetrafluoroethylene.

It is known that polytetrafluoroethylene is a material which is only very slightly thrombogen. However, the invention's merit lies in the fact that this material has been chosen as presenting a proven sufficient flexibility to effect transverse expansion of the flexible bands pre-cut-out on its periphery.

The filter-catheter according to the invention preferably comprises towards its distal end no other material than the polytetrafluoroethylene in contact with the blood flow. In that case, the tube and the inner conduit are joined by thermo-welding.

However, it is desirable to be able to follow the penetration and placing of the catheter inside the vein. To that end, it is known to employ a radio-opaque element near the filtering element. In the present case, the filter-catheter comprises a ring made of a radio-opaque material, for example gold, which is included between the tube and the inner conduit and fixed thereto during thermo-welding.

In this way, this radio-opaque element is not visible and cannot be a source either of catching on the wall of the vein nor of possible formation of blood clots.

It has been observed that, after a prolonged dwell time in the vein, the flexible polytetrafluoroethylene bands, opened out transversely, underwent a deformation under the effect of the inherent weight of the filtering assembly. Such deformation is manifested in the form of a greater spacing apart of the lowermost bands and therefore a collapse of the filter, which causes a non-homogeneous distribution of the bands in the transverse section of the vein and in particular which brings about phenomena of turbulence of the blood flow around certain bands, fit for the appearance of blood clots.

In order to overcome this drawback, at least the distal part of the filter-catheter according to the invention is subjected to a prior thermosetting, the purpose of which is to increase the mechanical resistance to deformation of the flexible bands of polytetrafluoroethylene. This thermo-setting treatment may consist for example of baking in a micro-wave oven for 4 to 5 minutes.

During this thermo-setting, the flexible bands are preferably positioned in their opened out state. In this way, the polytetrafluoroethylene undergoes a sort of tempering which memorizes this opened out state in the polymeric structure of the material.

According to another version, the tube is held upstream of the notches and the tube downstream of the notches is subjected to a rotation on itself so as to give the flexible bands a twisted form, then a heat treatment is applied on the distal part of the filter-catheter in this configuration, the flexible bands being either at rest or in the opened out state. In this case, during use of the filter-catheter, the flexible bands naturally resume the helical form.

BRIEF DESCRIPTION OF THE DRAWINGS

The invention will be more readily understood on reading the following description with reference to the accompanying drawings, in which.

DETAILED DESCRIPTION OF THE DRAWINGS

Figure 1:
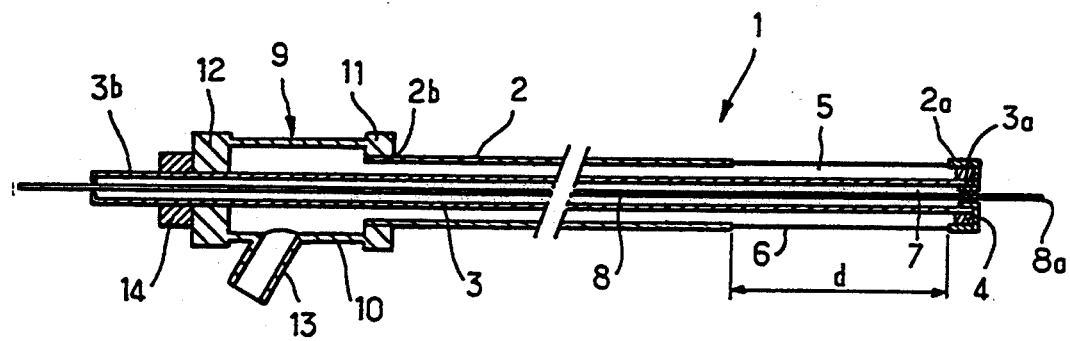
FIG. 1 is a schematic view, in section, of the filter at rest.

Referring now to the drawings, the filter-catheter 1 of the invention is essentially composed of a hollow tube 2 and of a hollow conduit 3 which is placed coaxially inside tube 2. These two elements, tube 2 and conduit 3, are made of polytetrafluoroethylene.

In the present specification, the terms "proximal" and "distal" are employed, taking as reference the part of the patient's body through which the filter is introduced. The distal end of the filter, shown to the right in FIGS. 1 and 2, is thus the end most remote from that part of the body, and the proximal end is the closer one.

The distal ends, 2a of tube 2 and 3a of conduit 3, respectively, are thermo-welded together and around a metal ring 4, made of stainless steel, platinum or gold. This ring 4 is made of a radio-opaque material, detectable during positioning of the filter.

Figure 2:
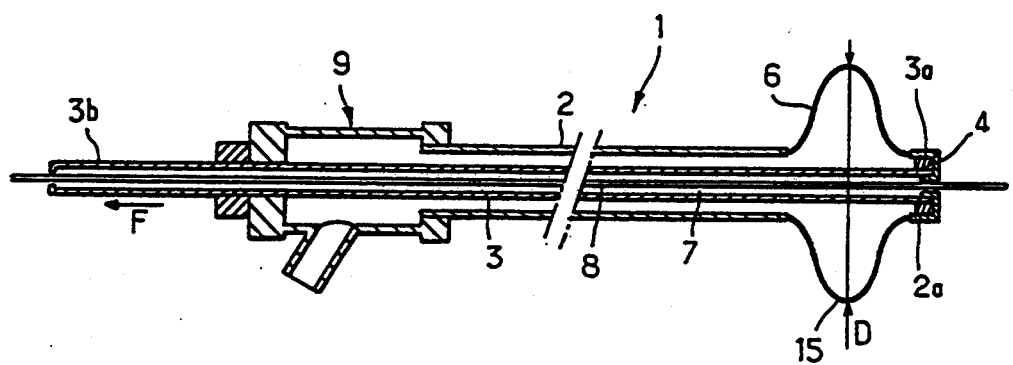
FIG. 2 is a schematic view, in section, of the filter opened out.

As is clearly shown in FIGS. 1 and 2, the ring 4 is placed between tube 2 and the distal end 3a of conduit 3, the distal end 2a of the tube being bent inside conduit 3 and covering the distal end 3a of said conduit. These elements are thermo-welded together to form the end 15 of the filter-catheter.

Figure 4:
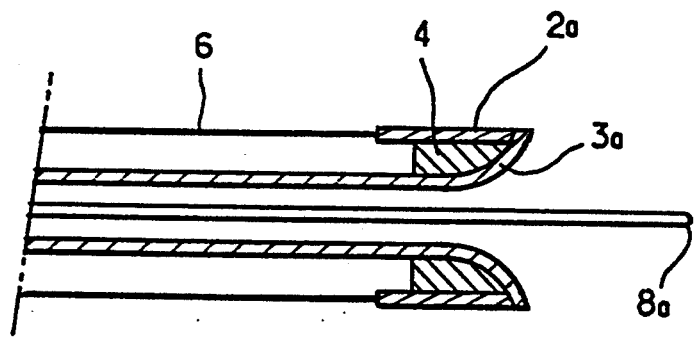
FIG. 4 is a schematic view, in section, of the distal end of a filter.

According to another embodiment illustrated in FIG. 4, thermo-welding occurs while the distal end 3a of the inner conduit 3 projects beyond the metal ring 4 and flares outwardly, coming into contact with the distal end 2a of tube 2.

Upstream of its distal end 2a, tube 2 comprises six notches 5, made in the longitudinal direction over a length d of 30 mm; they are regularly distributed over the periphery of the tube. These notches 5 define six identical bands 6, each occupying an angular space of 60° of the tube 2. For a tube 2 with a diameter of 3 mm, each band 6 has a width of about 1.5 mm.

The conduit 3 is hollow and comprises a central channel 7, in which a metal rod 8 serving as guide rod during introduction of the filter-catheter, may freely slide.

Towards the proximal end, but outside the patient's body, the tube 2 is fixed to a device 9 for maintaining and for supply. This device 9 comprises a cylindrical tube 10 and end rings 11 and 12. The first annular ring 11 joins the proximal end 2b of tube 2 to the front part of tube 10. The second ring 12 surrounds conduit 3 and closes the rear part of the tube 10. An elbow 13 opens out obliquely in the body of the tube 10.

The proximal end 3b of conduit 3 extends beyond tube 10. Ring 12 hermetically surrounds this distal end 3b; however, conduit 3 may slide longitudinally in ring 12 with respect to tube 10 and therefore to tube 2.

A blocking ring 14 blocks conduit 3 against ring 12.

Tube 10 is fixed in known manner near the patient on a frame supporting two systems for supply of products to be injected, opening out, for the first, in the proximal end 3b of the conduit and, for the second, in the elbow 13 of tube 10.

The filter-catheter functions under the following conditions:

In a first phase, the guide rod 8 is introduced by the percutaneous route into the appropriate vein, until its distal end 8a is in position in the patient's inferior vena cava.

In a second phase, the filter-catheter 1 is slid from outside the patient's body along the guide rod 8 until the ring 4 is in position in the vena cava, where the filter is to be implanted.

While this second phase is being carried out, the bands 6 are at rest, i.e. they are in line with the tube 2.

In a third phase illustrated in FIG. 2 and corresponding to the opening out of the filter, the blocking ring 14 is loosened so as to allow conduit 3 to slide in ring 12. The proximal end 3b of conduit 3 is then displaced with precaution rearwardly in the direction of arrow F. In this phase, the whole of conduit 3 moves as well as ring 4, fast with the distal end 3a of the conduit. Being given that tube 10 and therefore tube 2 are maintained in position, the ring 4 can move back in the direction of arrow F only thanks to the presence of the flexible bands 6. Each band 6 folds individually, consequently creating a homogeneous transverse deformation of the tube in the zone of notches 5. The displacement and length of the bands 6 are chosen so that, in opened out position, the median parts 15 of the bands 6, corresponding to plan D of curvature, abut on the inner wall 16 of the vein. Once the filter is correctly opened out, the blocking ring 14 is tightened so as to prevent any displacement of conduit 3 with respect to tube 2 and therefore to maintain the bands 6 in their state of transverse deformation.

Figure 3:
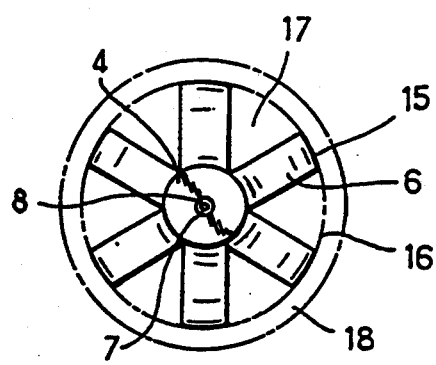
FIG. 3 is a view in transverse cross section of the filter along axis D of FIG. 2.

As is clearly apparent in FIG. 3, which is a section along plane D, the six bands 6 are opened out transversely with respect to tube 2 and partially obturate the interior 17 of the vein 18. In this way, the blood clots moving inside (17) the vein 18 are stopped by the bands 6 whilst the blood can circulate freely.

Prior to the use of the filter,catheter, the latter was subjected to a heat treatment of thermosetting. This treatment consisted in giving a thermal shock to the distal part of the filter while the flexible bands 6 are in their opened out state, as illustrated in FIG. 2. The duration of this treatment and the temperature are determined so that the shape taken by the bands is to some extent memorized in the polymeric structure of the polytetrafluoroethylene. This treatment increases the resistance of the bands 6 to deformation and avoids collapse of the filter inside the vein 18 and the risk of thrombogenesis due to the turbulences created in the blood flow by the heterogeneous arrangement of the bands 6 in the vein.

Figure 5:
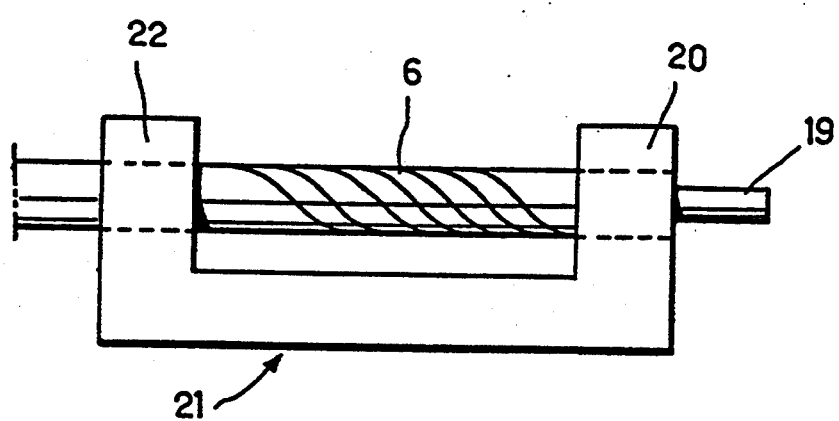
FIG. 5 is a schematic side view of the device for holding the filter-catheter during the thermosetting treatment.

According to another embodiment of the thermosetting treatment illustrated in FIG. 5, the heat treatment is applied on the distal part of the filter-catheter while the flexible bands 6 have a twisted form. To that end, a mandrel 19 is fitted in the inner conduit 3 so as to rigidify the distal part of the filter-catheter; the distal end 2a of tube 2 is blocked in position in the front leg 20 of a holding support 21; tube 2 is subjected to a rotation on itself, which gives the flexible bands 6 the twisted shape illustrated in FIG. 5; then tube 2 is blocked in position upstream of said flexible bands 6 in the rear leg 22 of the support 21. The support 21 and the distal part of the filter-catheter are placed in a baking oven, for example a micro-wave oven, in order to undergo the thermal treatment for 4 to minutes. It will be noted that, during use of the filter, the flexible bands 6 tend to take the helical form given during the thermal treatment. On support 21, the bands 6 may of course be in the rest position as shown in FIG. 5 or in the opened out state.

A product for therapeutic treatment may be injected upstream of the filter through conduit 3, from the proximal end 3b thereof. This is an anti-coagulant of the heparin type or a fibrinolytic. The conduit 3 may comprise orifices, for example disposed spirally, in the zone opposite bands 6. In this way, the product for therapeutic treatment introduced into conduit 3 may be distributed both upstream and at the level of the filter itself.

The same product, or possibly another product for therapeutic treatment, may be injected into the zone immediately downstream of the filter through tube 2, from the elbow 13 of tube 10.

Figure 6:
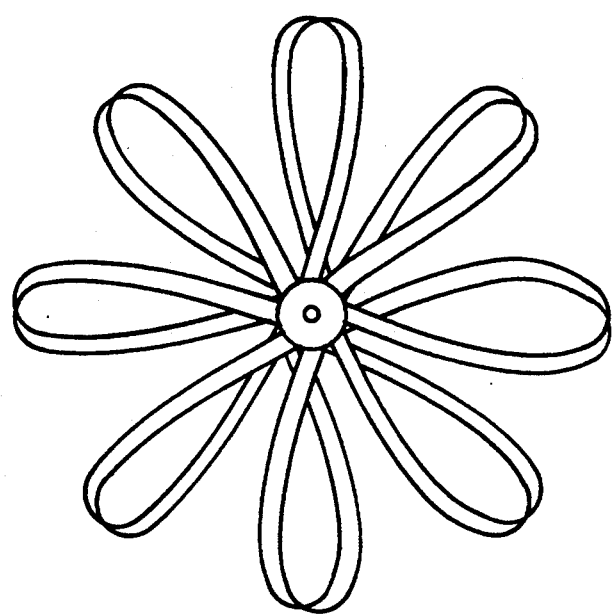
FIG. 6 is a schematic front view of the distal end of the filter in which the flexible bands have a helical shape.

When the treatment of thermositting has been effected while the bands were helically twisted, and consequently when the flexible bands have a helical shape as illustrated in FIG. 6, the filtration has the best results. Small blood clots are stopped by the helically shaped bands more surely than by the bands which are not helically shaped.

This helical configuration is obtained merely by the treatment of thermositting on the distal part of the filter. It is very advantageous. Indeed it would be possible to form helical slits in the distal part, but it was technically much more difficult than making longitudinal slits. Also it would be possible to have the tube turned while the inner conduit is stationary, but complementary mechanical means were necessary.

Once the treatment is judged satisfactory, the filter is withdrawn in the following manner: the blocking ring 14 is loosened and the proximal end 3b of conduit 3 is pushed in the direction opposite arrow F until the bands 6 resume their position of rest, rectilinear and parallel to one another. The ring 14 is then tightened again, and the conduit 3/tube 2 assembly is withdrawn from the vein.

Tests run with the filter-catheter according to the invention have made it possible to observe the absence of any formation of blood clots due to the presence of the filter in the vein.

The present invention is not limited to the embodiment which has been described by way of non-limiting example, but covers all the variants thereof. In particular, the guide rod 8 may be hollow and allow the injection of product for treatment downstream of the filter and even well beyond the distal end of the filter-catheter 1.

What is claimed is:

1. A method of manufacturing a filter/catheter device comprising the steps of:

providing a tubular outer tube made of polytetrafluoroethylene and arranging in the outer tube a series of longitudinal slits formed symmetrically around the periphery thereof adjacent the distal end of the tube so as to define a series of parallel narrow flexible bands therebetween, inserting an inner conduit slidable within said outer tube made also of polytetrafluoroethylene, the inner conduit being extended to the distal end of the outer tube and fastened therebetween at that point only, rotating slightly the proximal end relative to the distal end of the tube so that the flexible bands are twisted into a helical or spiral pattern, then retracting said inner conduit relative to said outer tube proximal end such that the distal end will be brought closer to said proximal end thereby expanding the pattern of helical flexible bands radially outwardly of the outer tube, briefly heat treating the expanded helical bands for a short time at a low temperature, thereafter cooling the device to maintain the bands in said helical shape, and then extending said conduit outwardly in said outer tube in order to stretch the helical bands from their expanded outward position to a normal storage position so that the bands return to their original position along said outer tube.

* * * * *